US009990861B2

(12) United States Patent
Chichilnisky et al.

(10) Patent No.: US 9,990,861 B2
(45) Date of Patent: Jun. 5, 2018

(54) SMART PROSTHESIS FOR FACILITATING ARTIFICIAL VISION USING SCENE ABSTRACTION

(71) Applicants: Eduardo-Jose Chichilnisky, Palo Alto, CA (US); Martin Greschner, Oldenburg (DE); Lauren Jepson, San Diego, CA (US)

(72) Inventors: Eduardo-Jose Chichilnisky, Palo Alto, CA (US); Martin Greschner, Oldenburg (DE); Lauren Jepson, San Diego, CA (US)

(73) Assignee: Pixium Vision (FR)

(*) Notice: Subject to any disclaimer, the term of this patent is extended or adjusted under 35 U.S.C. 154(b) by 695 days.

(21) Appl. No.: 14/289,457

(22) Filed: May 28, 2014

(65) Prior Publication Data

US 2014/0375782 A1 Dec. 25, 2014

Related U.S. Application Data

(60) Provisional application No. 61/828,124, filed on May 28, 2013.

(51) Int. Cl.
*G09B 21/00* (2006.01)
*A61N 1/36* (2006.01)
(Continued)

(52) U.S. Cl.
CPC ........ *G09B 21/008* (2013.01); *A61N 1/36046* (2013.01); *G06K 9/00671* (2013.01); *G06T 11/001* (2013.01); *H04N 5/272* (2013.01)

(58) Field of Classification Search
CPC .............. G09B 21/008; A61N 1/36046; G06K 9/00671
(Continued)

(56) References Cited

U.S. PATENT DOCUMENTS 5,944,747 A  8/1999  Greenberg et al.
6,432,050 B1  8/2002  Porat et al.
(Continued)

FOREIGN PATENT DOCUMENTS

JP  2005-279002  10/2005
WO  WO 2012/129175  9/2012
WO  WO 2014/193990  12/2014

OTHER PUBLICATIONS

International Search Report and Written Opinion for International Application No. PCT/US2014/039844, dated Sep. 23, 2014, 16 pages.
(Continued)

*Primary Examiner* — Jeffery Williams
(74) *Attorney, Agent, or Firm* — Cooley LLP

(57) ABSTRACT

A method of providing artificial vision to a visually-impaired user implanted with a visual prosthesis. The method includes configuring, in response to selection information received from the user, a smart prosthesis to perform at least one function of a plurality of functions in order to facilitate performance of a visual task. The method further includes extracting, from an input image signal generated in response to optical input representative of a scene, item information relating to at least one item within the scene relevant to the visual task. The smart prosthesis then generates image data corresponding to an abstract representation of the scene wherein the abstract representation includes a representation of the at least one item. Pixel information based upon the image data is then provided to the visual prosthesis.

34 Claims, 15 Drawing Sheets

(51) Int. Cl.
*H04N 5/272* (2006.01)
*G06K 9/00* (2006.01)
*G06T 11/00* (2006.01)

(58) Field of Classification Search
USPC .......................................................... 348/62
See application file for complete search history.

(56) References Cited

U.S. PATENT DOCUMENTS

| | | |
|---|---|---|
| 2002/0193845 A1 | 12/2002 | Greenberg et al. |
| 2004/0030383 A1 | 2/2004 | Havey et al. |
| 2005/0004625 A1 | 1/2005 | Chow |
| 2005/0288734 A1 | 12/2005 | Greenberg et al. |
| 2006/0135862 A1 | 6/2006 | Tootle et al. |
| 2008/0046031 A1 | 2/2008 | Greenberg et al. |
| 2008/0086206 A1 | 4/2008 | Nasiatka et al. |
| 2009/0281451 A2 | 11/2009 | Hetling et al. |
| 2010/0063498 A1 | 3/2010 | Kaushal et al. |
| 2010/0220176 A1* | 9/2010 | Ziemeck ............ A61N 1/36046 348/50 |
| 2010/0241192 A1 | 9/2010 | Greenwald et al. |
| 2012/0109295 A1 | 5/2012 | Fan |
| 2013/0035742 A1 | 2/2013 | Talbot et al. |
| 2013/0131985 A1* | 5/2013 | Weiland ................. G01C 21/20 701/516 |
| 2013/0187835 A1* | 7/2013 | Vaught ............... G06K 9/00604 345/8 |
| 2014/0121724 A1 | 5/2014 | Chichilnisky et al. |

OTHER PUBLICATIONS

Office Action for U.S. Appl. No. 14/005,818, dated Aug. 27, 2015, 20 pages.
Supplementary European Search Report for European Application No. 12760531.9, dated Aug. 12, 2014, 7 pages.
International Search Report and Written Opinion for International Application No. PCT/US2012/029683, dated Jul. 17, 2012, 11 pages.
Petrusca, D. et al., "Identificaiton and characterization of a Y-like primate retinal ganglion cell type," The Journal of Neuroscience, Oct. 10, 2007, 27(41):11019-11027.
Greschner, M. et al., "Correlated firing among major ganglion cell types in primate retina," The Jornal of Physiology, 589.1 (2011):75-86.

* cited by examiner

SMART PROSTHESIS FOR FACILITATING ARTIFICIAL VISION USING SCENE ABSTRACTION

CROSS REFERENCE TO RELATED APPLICATIONS

This application claims priority to and the benefit of U.S. Provisional Patent Application No. 61/828,124, entitled "SMART PROSTHESIS FOR FACILITATING ARTIFICIAL VISION USING SCENE ABSTRACTION" filed May 28, 2013, the disclosure of which is incorporated herein by reference in its entirety.

FIELD OF THE INVENTION

The systems and methods disclosed herein relate to visual prostheses. In particular, but not by way of limitation, the disclosure relates to systems and methods for enhancing the capabilities of retinal prostheses.

BACKGROUND OF THE INVENTION

Now and for the foreseeable future, retinal prostheses for treating blindness are expected to possess extremely low bandwidth, i.e. pixel resolution, compared to the native capacities of a visual system including an intact retina. Thus, efforts have been made to improve the performance of retinal prostheses by operating on the pixel values produced by their imaging cameras using standard image processing techniques. Unfortunately, such efforts have not improved such prostheses to the extent necessary to enable them to become useful in providing substantial assistance to visually-impaired users desiring to engage in various everyday tasks (e.g., navigating stairs, recognizing faces, counting money). These efforts may have been hindered at least in part because the pixel intensities registered by such cameras tend to be dominated by idiosyncratic information that is largely irrelevant to the visually-impaired user in view of the task at hand.

SUMMARY

In view of these shortcomings of existing retinal prostheses, it is believed that extraction of task-relevant information and efficient representation of that information requires an entirely different approach to representing information about the external world to visually-impaired patients or users. To this end, the present disclosure describes an intelligent or "smart" prosthesis preferably configured to perform advanced processing on input image information from a camera and potentially other information sources to produce an abstracted representation of the visual world. Based upon this abstracted representation, the smart prosthesis produces pixel values which, when used to stimulate the retina of a visually-impaired user, produce for the user a simplified, abstracted image well-suited for various tasks desired to be performed by the user.

In one aspect, the disclosure is directed to an improved method and apparatus for presenting image data to a visually-impaired user using a visual prosthesis. In one embodiment the disclosed smart prosthesis extracts high-level abstracted information about a scene in real-time using advanced computational techniques. This contrasts with standard methods for driving a visual prosthesis, which rely upon relaying raw or filtered pixel camera video to the user. The abstracted scene information is then presented, either alone or integrated with some or all of the camera video or other input image information, in a simplified and abstracted fashion. This results in presentation of a more intelligible and useful representation of the user's surroundings to the user, thus enabling the user to productively engage in visual tasks previously incapable of being performed.

The smart prosthesis system may include one or more cameras and other sensors and a processor residing on an Internet-connected smartphone or similar device. The image data produced by the smart prostheses is useable to drive an array of electrodes or optical system to stimulate the retina.

During operation of the smart prostheses, a user may select one of a plurality of aides, for instance people recognition, reading, navigation, or shopping. Each aide may integrate information from the Internet and databases with information extracted from the live video stream or other imagery produced by the camera and other sensors of the prostheses in order to produce a representation of people, objects and locations. This enables the user to be presented with an abstracted and potentially augmented view of a surrounding visual scene, optimized for the task at hand and the resolution available on the prosthesis.

In one aspect, the disclosure relates to a method of providing artificial vision to a visually-impaired user implanted with a visual prosthesis. The method includes configuring, in response to selection information received from the user, a smart prosthesis to perform at least one function of a plurality of functions in order to facilitate performance of a visual task. The method further includes extracting, from an input image signal generated in response to optical input representative of a scene, item information relating to at least one item within the scene relevant to the visual task. The smart prosthesis then generates image data corresponding to an abstract representation of the scene wherein the abstract representation includes a representation of the at least one item. Pixel information based upon the image data is then provided to the visual prosthesis.

In another aspect the disclosure pertains to a method of providing artificial vision to a visually-impaired user implanted with a visual prosthesis. The method includes configuring, in response to selection information received from the user, a smart prosthesis to perform at least one function of a plurality of functions in order to facilitate performance of a visual task. The method further includes extracting, from an input image signal generated in response to optical input representative of a scene, item information relating to at least one item within the scene relevant to the visual task. The smart prosthesis then creates an abstract representation of the scene wherein the abstract representation includes a representation of the at least one item. Augmented image data is then generated wherein the augmented image data includes at least a portion of the input image signal and abstracted data corresponding to the abstract representation. pixel information based upon augmented image data is then provided to the visual prosthesis.

The disclosure is further directed to a method of providing artificial vision to a visually-impaired user implanted with a visual prosthesis. The method includes producing an input image signal in response to optical input representative of a scene. The method further includes recognizing, by processing the input image signal, at least one item within the scene. Image data corresponding to an abstract representation of the scene is then generated wherein the abstract representation includes a symbolic representation of the at least one item. Pixel information based upon the image data is then provided to the visual prosthesis.

In yet another aspect, the disclosure relates to a method of providing artificial vision to a visually-impaired user implanted with a visual prosthesis. The method includes producing an input image signal in response to optical input representative of a scene. The method further includes recognizing, by processing the input image signal, at least one item within the scene. An abstract representation of the scene is then created wherein the abstract representation includes a symbolic representation of the at least one item. Augmented image data is generated wherein the augmented image data includes at least a portion of the input image signal and abstracted data corresponding to the abstract representation. The method also includes providing, to the visual prosthesis, pixel information based upon the augmented image data.

The disclosure is also directed to a method of assisting a visually-impaired user in performing a visual task. The method includes receiving information relating to one or more actions performed by the user. The method further includes determining the visual task based upon the one or more actions. An input image signal generated in response to optical input representative of a scene is received and item information relevant to the visual task is extracted from the input image signal. The method also includes generating, based at least in part upon the item information, image data corresponding to an abstract representation of the scene. Pixel information based upon the image data is provided to a visual prosthesis of the user.

In an additional aspect the disclosure pertains to a smart prosthesis including a processor and at least a video input device. The smart prosthesis further includes a non-transitory machine readable medium including instructions for execution by the processor. The instructions include instructions for receiving an input video signal produced by the video input device in response to optical input representative of a scene. The instructions further provide for recognizing, by processing the input video signal, at least one item within the scene. Image data corresponding to an abstract representation of the scene is then generated, where the abstract representation includes a symbolic representation of the at least one item. Pixel information based upon the image data is then provided to a visual prosthesis of the user.

The disclosure is also directed to a smart prosthesis for use by a visually-impaired user. The smart prosthesis includes a processor and non-transitory machine readable medium including instructions for execution by the processor. The instructions include instructions for receiving an input image signal produced in response to optical input representative of a scene. The instructions further provide for recognizing, by processing the input image signal, at least one item within the scene. Image data corresponding to an abstract representation of the scene is then generated wherein the abstract representation includes a symbolic representation of the at least one item. The method further includes providing, to a visual prosthesis of the user, pixel information based upon the image data.

In another aspect the disclosure pertains to a smart prosthesis for use by a visually-impaired user in performing a visual task. The smart prosthesis includes a processor and a non-transitory machine readable medium including instructions for execution by the processor. The instructions include instructions for configuring, in response to selection information received from the user, a smart prosthesis to perform least one function of a plurality of functions in order to facilitate performance of a visual task. The instructions further provide for extracting, from an input image signal generated in response to optical input representative of a scene, item information relating to at least one item within the scene relevant to the visual task. In addition, the instructions include instructions for generating, by the smart prosthesis, image data corresponding to an abstract representation of the scene wherein the abstract representation includes a representation of the at least one item associated with the item information. The instructions further include instructions for providing, to a visual prosthesis of the user, pixel information based upon the image data.

In yet an additional aspect, the disclosure is directed to a smart prosthesis for assisting a visually-impaired user in performing a visual task. The smart prosthesis includes a processor and a non-transitory machine readable medium including instructions for execution by the processor. The instructions include instructions for receiving information relating to one or more actions performed by the user. The instructions further include instructions for determining the visual task based upon the one or more actions and receiving an input image signal generated in response to optical input representative of a scene. The instructions also provide for extracting, from the input image signal, item information relevant to the visual task and generating, based at least in part upon the item information, image data corresponding to an abstract representation of the scene. The instruction further cause pixel information based upon the image data to be provided to a visual prosthesis of the user.

The embodiments summarized above are more fully described in the Detailed Description section. It is to be understood, however, that there is no intention to limit the disclosure to the forms described in this Summary or in the Detailed Description. One skilled in the art can recognize that there are numerous modifications, equivalents and alternative constructions that fall within the spirit and scope of the disclosure as expressed in the claims.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings wherein:

Figure 1:
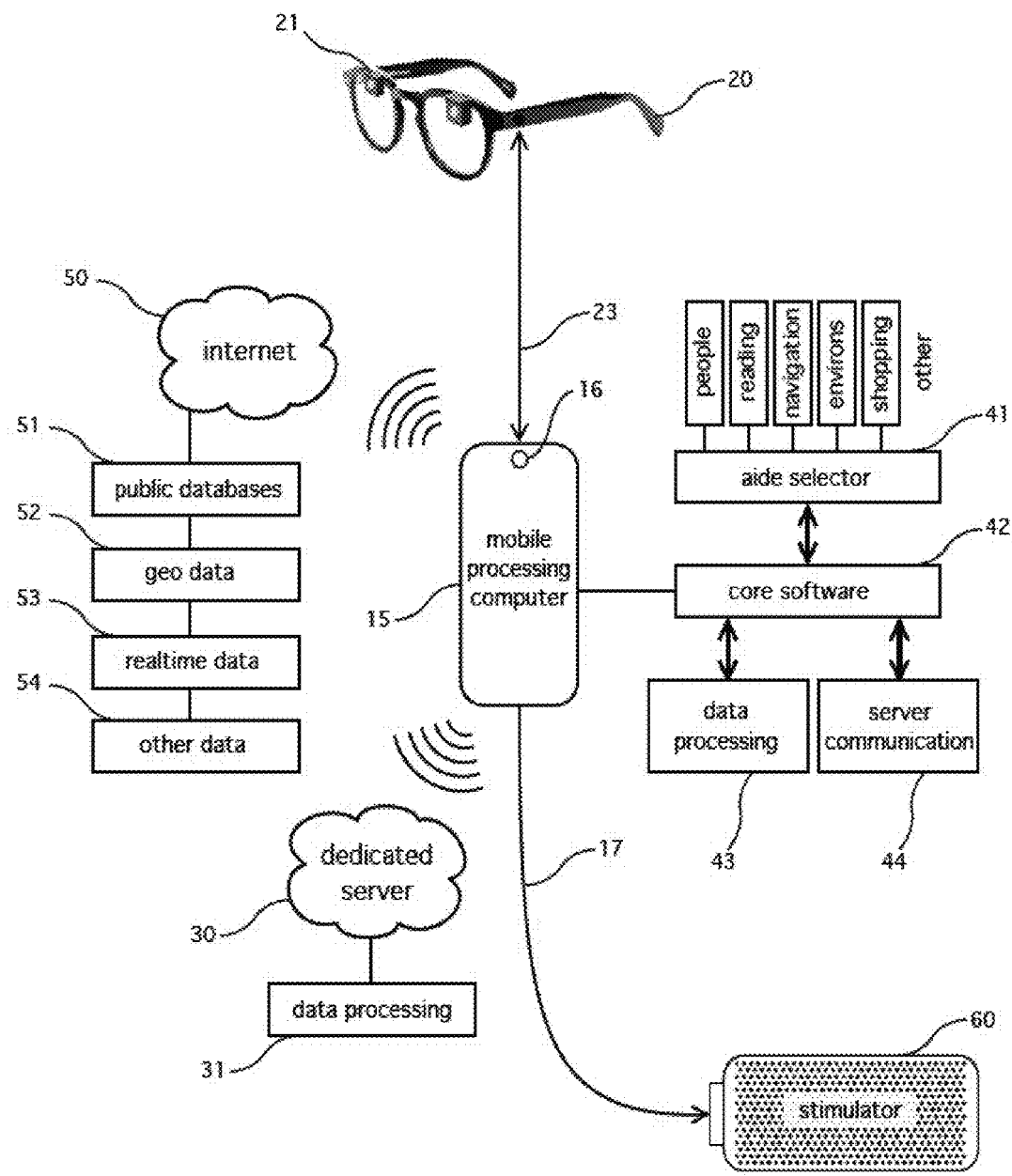
FIG. 1 is a block diagram depicting components of a smart prosthesis system.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

As is discussed more fully below, the smart prosthesis described herein is generally not adapted to register veridically an approximation of a pixilated visual image incident on a camera, nor to mimic retinal processing, as do conventional visual prostheses. Rather, embodiments of the smart prostheses gather information about the external world of a user from a variety of sources (e.g., cameras, sensors, databases) to intelligently extract high-level information about people, objects and spatial relationships in a manner most relevant to a task being performed by a user. This information may then be processed into a stream of pixel values useable to stimulate retinal neurons in a way that creates an abstracted but meaningful artificial image of the world and efficiently uses the limited number of available stimulation sites.

To create a useful visual representation, in one embodiment the smart prosthetic device gathers information about the world and the user's relationship to it using a variety of sensors, primarily a camera, but also potentially others such as a compass, accelerometer, GPS, and gyroscope. The smart prosthesis may be configured to focus on parts of the world indicated by the user's eye movements and other actions identified with sensors. Using information from, for example, the user's digital assistant, camera, computers and, potentially, Internet resources, the smart prosthetic may identify objects and people and their locations, and relate them to objects and people and locations known to or of interest to the user. This information is then used to create an abstracted representation of the aspects of the environment most relevant to the current activities of the user, such as navigating, reading, shopping, and interacting with objects and people. The smart prosthetic device preferably senses the user's current activity and intentions using a combination of gestures and automation, and uses this information to produce an abstracted representation of the visual scene that emphasizes the features relevant for the activity. This representation is transmitted to the stimulators on the device with knowledge of the properties of the stimulators and information about the percepts they generate in the user, creating an artificial image for the user that most naturally and effectively enables the chosen activity.

An illustrative example is navigation. The user's location in space may be determined coarsely with a GPS device in a smartphone, and fine-tuned with information from the camera and other sensors. Consultation with Internet databases may be used to produce a schematic representation of the user's surroundings, such as the main features of a particular intersection in a city. Camera information may also be used to identify the major obstacles in the environment not present in databases, such as cars and other movable objects. This information is then combined with the user's selected destination to determine a safe and efficient route for movement. Specifically, in one embodiment the essential features of the environment identified by the device, such as streets and obstacles, are used to render a simplified line drawing of the local world and the path toward the destination, corrected according to the user's heading and eye movements. No attempt is made to reproduce all of the pixel intensities registered by the camera, which largely reflect factors such as illumination, texture, and color that are irrelevant to the task of navigation.

Referring now to the drawings, where like or similar elements are designated with identical reference numerals throughout the several views, and referring in particular to FIG. 1, which illustrates an overview of the disclosed smart prosthesis. As shown, the smart prostheses may include a mobile processing device 15 (e.g., a smartphone) running core software 42. The processing device 15 is connected via a wired or wireless connection 23 to eye glasses 20 containing input devices 21 including, for example, a camera of video camera. The core software 42 further features a selector 41 with access to various aide functions, described in detail below. An array of visual and non-visual sensors 16 reside on the processing device 15 as well as on the glasses 20. In one embodiment one or more input devices of the smartphone 15, such as a camera, are utilized in addition to, or in lieu of, the input devices 21 of the eye glasses 20.

The processing device 15 preferably communicates wirelessly with the Internet 50 and a dedicated server 30 using server communications software 44. This allows access to a multitude of databases 51, data resources 52-54, and server-connected data processors 31.

For most functions carried out by the smart prosthesis system, a live server data connection is assumed. However, core software residing on the smartphone is capable of significant data processing 43, enabling the device to function in an off-line mode requiring no network connectivity. When applicable, functions available for stand-alone, local computation are noted below.

The mobile processing device 15 features a wired or wireless connection 17 to an implanted retinal stimulator. During operation, the output of the smart prosthesis system is provided as an input to the retinal stimulator. As a consequence, specific implementations of the various embodiments described below will generally be dependent upon and influenced by the resolution and capabilities of the retinal stimulator.

Figure 2:
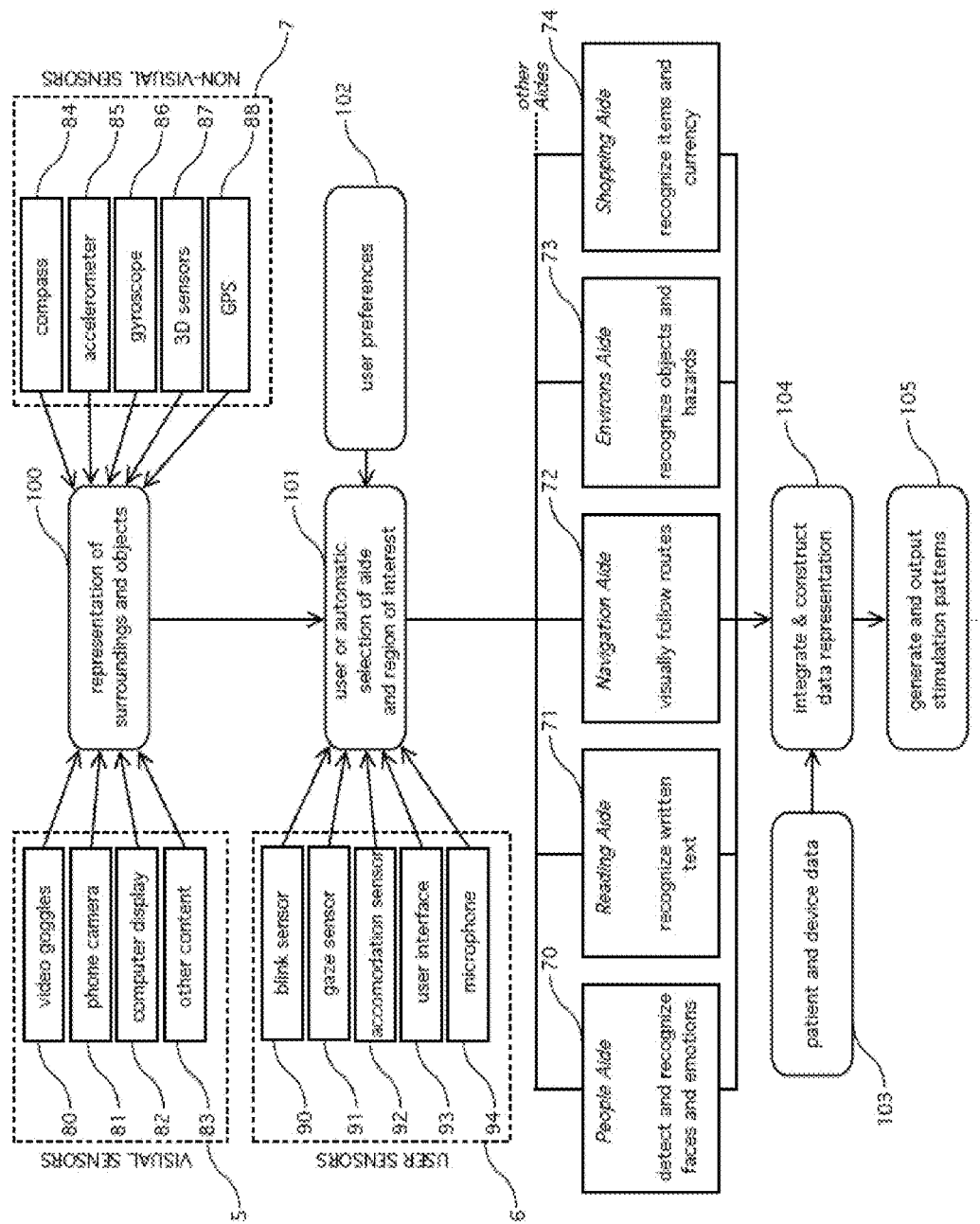
FIG. 2 is a flow chart showing the typical processing flow from input to output in a smart prosthesis.

FIG. 2 provides an overview of a typical data flow occurring within the smart prosthesis system. Various visual input sources, represented by Visual Sensors 5, provide input image data, such as video stream data. A main visual input is given by a single video camera or a set of video cameras 80. The main input can be combined with, or substituted by, other input sources. A hand held camera 81, such as one built into a smartphone, can be used as an additional input source. This allows for more convenient or flexible access to objects of interest, such as books and photos. The content of a digital display 82 rendered by a computer or smartphone, such as the processing device 15, can be used directly as an input source instead of being viewed indirectly via the video cameras. Other digital content 83 can also be used directly as input without being prepared for a display.

In one embodiment the smart prostheses contains an array of Non-visual Sensors 7 similar or identical to those employed by state-of-the-art mobile computing and gaming devices. The Non-visual Sensors 7 may include, for example, a compass 84, an accelerometer 85, one or several gyroscopes 86, 3D sensors 87 (such as a range imaging or depth sensors), and a GPS unit 88. The 3D sensing capabilities can be implemented by devices such as, for example, PrimeSense's Carmine/Capri 3D Sensors or APIs capable of producing detailed depth maps of any surface.

The input sources 80-88 are integrated to generate a representation of the surroundings and objects 100. State of the art image processing may be used to detect items or objects from the inputs and identify associated item information such as faces, text, barcodes, currencies and outlines of rooms and building. State-of-the-art augmented reality technology may be used to combine the sensors with the main video signal. Color and intensity information may be used in combination with 3D information from range imaging to segregate and detect physical objects.

As shown in FIG. 2, an additional set of sensors, i.e., User Sensors 6, may be provided to assist the user in interacting with the device. The User Sensors 6 may include a blink sensor 90 configured to detect eye blinks by the user, including their speed and length. This can be implemented by analyzing a secondary video image of the eye or by recording muscular potentials. Examples of available devices that could be utilized to realize the blink sensor 90 include, for example, AMDi's Fiber-Optic Eye-Blink Sensor and the Eye Blink Switch available from Enabling Devices. A gaze sensor 91 detects the direction of the user's gaze and the duration of fixation. This can be implemented by analyzing a secondary video image of the eye or by recording muscular potentials. Goggle-mounted mobile eye tracking systems are commercially available in the form of, for example, the Tobii Glasses by Tobii. An accommodation sensor 92 measures the accommodation of the user's lens (i.e. near or far focus). Additionally, a user interface 93 is used to provide miscellaneous user input. This interface can consist of physical buttons or appropriately designed touch screen applications. Finally, a microphone 94 enables the user to issue spoken commands. A combination of these sensors (90-94) can be used to define events that trigger certain behaviors of the device, for instance multiple blinks or blink patterns to change the zoom of the video input, fixation of gaze to activate a specific aide function, or distance focusing to shift between objects of interest.

As shown in box 101, the device selects specific aide functions 70-74 or regions of interest based on user inputs or on automated rules. For example, a long fixation on a particular region of a visual scene can define a region of interest. In this regard the "scene" may encompass not only the scene view provided by video goggles 80, a phone camera 81 or the like, but may also be defined in whole or part by inputs derived from other sources, e.g., the computer display 82, an Internet browser, bar code, etc.

If, in this region, an object is detected for which a particular aide is defined, this aide is activated as specified below. Certain objects can trigger specific aides automatically. For example, the detection of a known face might trigger the People aide. The detection of a nearby hazard for which the user has a low detection probability might trigger automatically the Environs Aide. The user can actively switch between video sensors 80-83, aides and regions of interest. The individual, task-specific aide functions 70-74 are described in detail below in conjunction with FIGS. 3-12.

The behavior and thresholds of the automatic selection, as well as the parameters of the user inputs, may be adjusted in a training phase 102 to accommodate the user's preferences, abilities and needs.

In one embodiment the output of each aide function 70-74 constitutes an abstracted rendering of the real world environment surrounding the user. For example, this abstracted rendering may be in the form of line drawings or text displays which are based upon the video or other image data produced by the Visual Sensors 5 but which do not incorporate any pixel data included within such image data. The output of an aide function 70-74 may then be subsequently integrated with the live video or image data produced by the Visual Sensors 5 in order to generate an augmented reality representation 104, resulting in an optimized, integrated data signal. In one embodiment the extent to which live video content is blended with abstracted content in generating an augmented reality representation 104 differs depending on which of the aide functions 70-74 is currently active. When applicable, this blend ratio is noted below in the discussion of the individual aide functions.

User and device information 103 are preferably taken into account for the construction of the optimized representation of the visual surrounding 104. This information includes data on the physical and stimulation properties of the given prostheses, as the number of electrodes, possible stimulation patterns and spatial extent. It also includes user data that describe the visual sensation that the user experiences for a given stimulation site or sites. As discussed above, after stimulator implantation these data are collected in an initial training phase 102. They are expected to change over time and may require readjustments. The user data might include spatial inhomogeneity resulting from imperfect implantation or inhomogeneity in the health of the user's retina. For every spatial location, a psychometric function is preferably stored, representing the user's percept at a given stimulation. Furthermore, the data include the spatial and temporal resolution of the user's percepts and the spatial form and distribution of the user's percepts.

The optimized representation is passed on to the stimulation module 105, which contains the driver unit for a retinal or other visual prosthesis to generate the necessary electrical stimulation patterns.

In more detail, five proposed aide functions 70-74 (FIG. 2) are described. Of course, these aide functions are merely exemplary and additional functions may be added to address other visual tasks. In one embodiment each aide function receives input from and has access to the data provided by the array of sensors 80-94, preferably including high-resolution video stream data. From these data, each aide function constructs a synthetic model of the outside world and provides this abstracted model to the user of the implant. Aides may also share a common data framework that captures aspects of the outside world useful for many or all aides. Each aide typically replaces raw camera images with simplified representations of the visual world which are tuned to the capabilities of the user's retinal or other visual implant and thus more intelligible to the user and useful for carrying out specific tasks.

Certain of the tasks executed by the individual aides in connection with performing an overall function may be carried out using currently available technologies or software applications. Examples of off-the-shelf application programming interfaces (APIs) that can be integrated into the smart prosthesis to facilitate execution of various tasks attendant to the performance of each aide function are described hereinafter.

Figure 3:
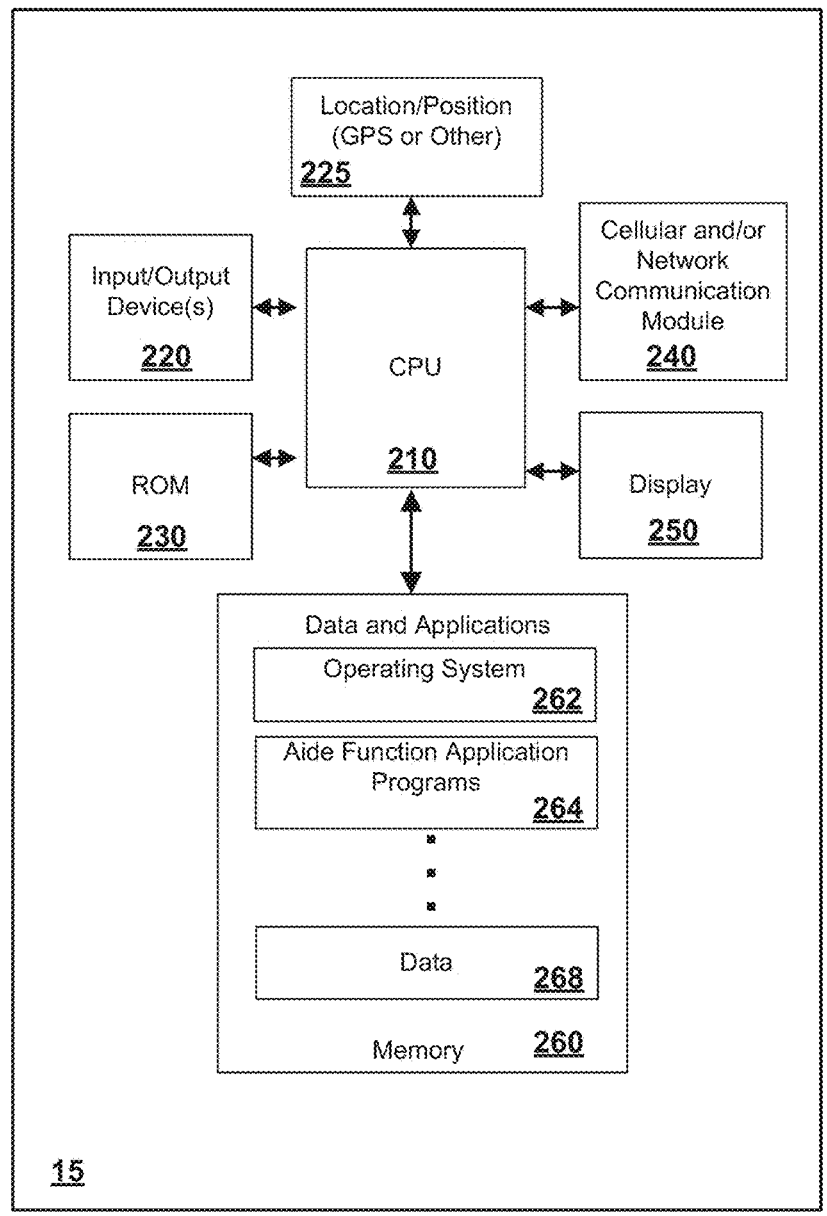
FIG. 3 illustrates additional details of a typical configuration of a processing device with example device elements that may be used to implement embodiments of the disclosed systems and methods.

Attention is now directed to FIG. 3, which illustrates additional details of a typical configuration of a processing device 15 with example device elements that may be used to implement embodiments of the disclosed systems and methods. As shown in FIG. 3, device 15 may include one or more processors (CPUs) 210, which are typically one or more specialized or dedicated portable device microprocessors or microcontrollers, an input/output device module 220 configured to allow users to input and output information and interact with applications installed on the device 15, such as applications corresponding to the aide functions 70-74, one or more read only memory (ROM) devices 230 or equivalents to provide non-volatile storage of data and/or application or operating system programs, one or more display modules 250, such as an LCD or equivalent display device, as well as one or more memory spaces 260 and phone camera 81. Other modules, such as optional GPS module 225 for providing position or location information may also be included.

Memory space 260 may comprise DRAM, SRAM, FLASH, hard disk drives or other memory storage devices configured to store and access operating systems 262, aide function application programs 264 and/or data 268. The aide function application programs 264 are disposed for execution on the CPU 210 to perform the various functionality described herein, including interacting with dedicated server 30 and input devices 21 of eye glasses 20.

Figure 4:
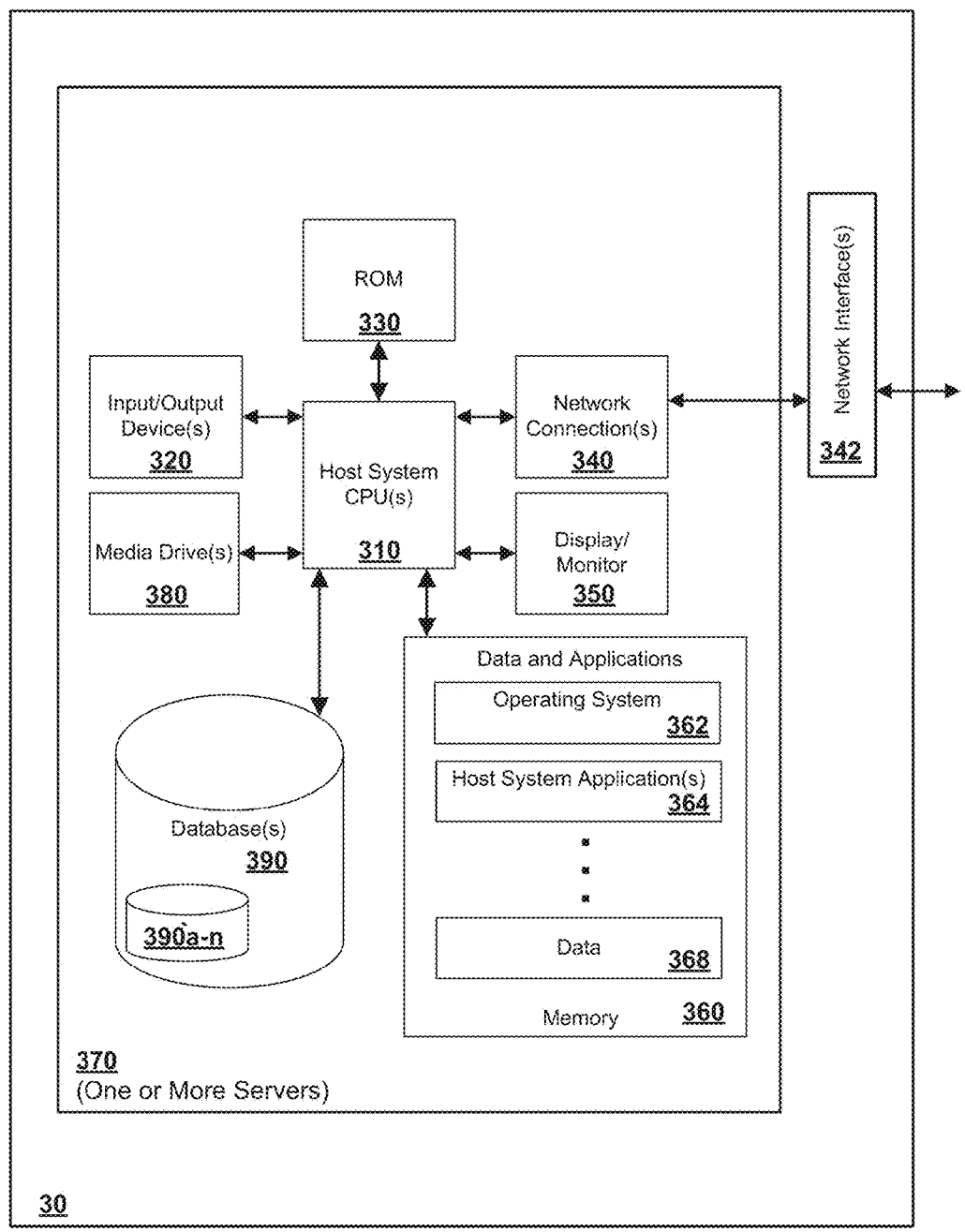
FIG. 4 illustrates additional details of one example of a dedicated server with exemplary device elements that may be used to implement embodiments of the present disclosure.

FIG. 4 illustrates additional details of one example of a dedicated server 30 with example device elements that may be used to implement embodiments of the present disclosure. As shown in FIG. 4, dedicated server 30 may include one or more processors (CPUs) 310, an input/output device module 320 configured to allow users to input and output information and interact with the dedicated server 30 as well as transfer and receive data, one or more read only memory (ROM) devices 330 or equivalents to provide non-volatile storage of data and/or programs, one or more display modules 350 such as a computer monitor or other display device, one more network connections 340 and associated network interfaces 342 configured to allow dedicated server 30 to connect to other systems, servers and/or portable devices, including other elements of system 140 in embodiments where the servers or other components are distributed at other physical locations, as well as one or more memory spaces 360 and one or more databases 390. Database(s) 390 may be further divided or distributed as one or more sub-databases 390a-390n, with the sub-databases storing feature or function specific information associated with a particular feature or function. The various components shown in FIG. 4 may be incorporated in one or more physical servers 370 comprising part of dedicated server 30. It is noted that the various components shown in FIG. 4, including database 390, are typically included as part of server(s) 370, however, they may be external to server(s) 370 in some embodiments. For example, in some embodiments database(s) 390 may be external to server(s) 370 and may comprise part of a separate database server system or networked database system.

Memory space 360 may comprise DRAM, SRAM, FLASH, hard disk drives or other memory storage devices, such as media drives 380, configured to store operating systems, application programs and/or data, and memory space 360 may be shared with, distributed with or overlap with the memory storage capacity of database 390. In some embodiments memory space 360 may include database 390 or in some embodiments database 390 may include data 368 as shown in memory space 360.

Data stored in memory space 360 and/or database 390 may include information such as images/photos of contacts or objects or other types of data. In particular, memory space 360 may include a host system application or applications 364 stored in the memory space for execution on CPU 310 to further support operation of the aide function application programs 264.

Attention is now directed to FIGS. 5-14, to which reference will be made in describing the processing and other operations involved in performing the aide functions 70-74

People Aide

A primary function of the People Aide 70 is to detect, identify, and recognize faces and provide a simplified representation of the results to the implant user in real-time so as to enable the user to interact and converse with others. Complex facial information is thus replaced by a symbolic depiction of people known or unknown to the user and their facial expressions. A flowchart representative of the operations performed by an exemplary implementation of the People Aide 70 is shown in FIG. 5.

Figure 5:
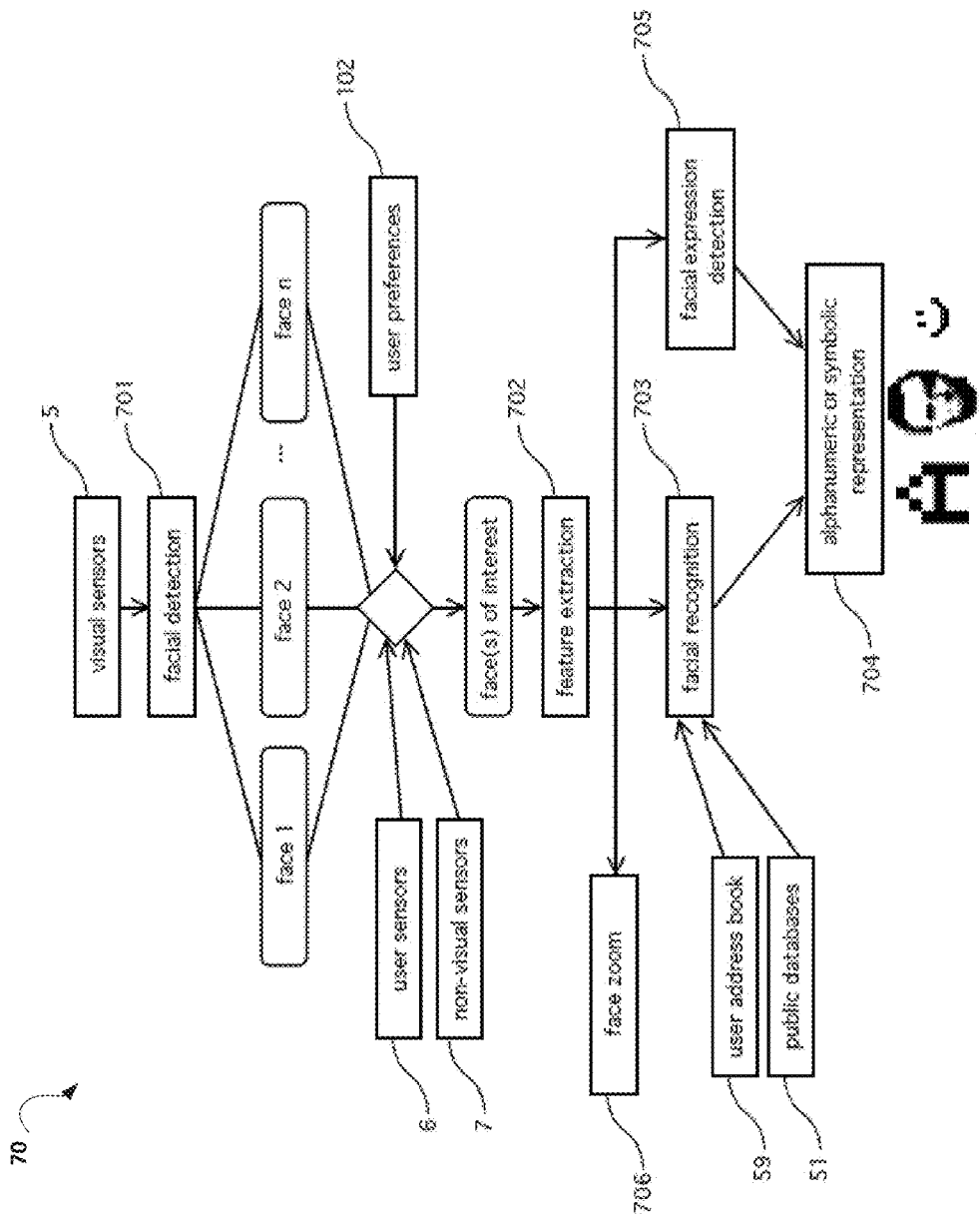
FIG. 5 is a flow chart depicting the function of the People Aide.

Referring to FIG. 5, visual sensor data 5 is subjected to frame-by-frame analysis by the facial detection module 701. This processing task 701 may be implemented using available solutions accessed through APIs integrated into the software application for the People Aide 70 instantiated on the processing device 15. Examples include the CIFaceFeature class in the iOS framework for facial detection in still or video images, or the FaceDetector API in Android.

In one embodiment, data from the user sensors 6 and non-visual sensors 7 are used to determine upon which face the user is currently focused. Examples of sensors which may be used in this task include the gaze sensor 89, accommodation sensor 90, and 3D depth sensor 87 (FIG. 2). Subsequent data processing is then limited to the most likely face of interest to the user. In another embodiment, all detected faces are processed. In a further embodiment, the user may actively select a face for further processing.

For each face of interest, a feature extraction module 702 obtains facial features and relays feature data to a facial recognition module 703. Facial features may be compared to data stored in the user's address book 59 or other databases 51, such as public figure or celebrity databases. This processing step 703 may be carried out using cloud-based face recognition APIs such as Lambda Labs Face Recognition, SkyBiometry, or the cloud based face recognition service by BioEnable.

Upon request by the implant user, the output of the feature extractor 702 is sent to a facial expression detector 705. Its purpose is to derive the likeliest emotional state of the detected face. This task may be accomplished by using facial expression and mood recognition tools, such as the Noldus FaceReader or Emotional Imaging's Fi-Ni Reader.

Upon request by the implant user, the People Aide may perform face zoom 706. This action results in a magnified live view, which includes some raw pixel data, of the detected face for closer inspection by the user. In one embodiment, face zoom may be activated automatically by prolonged fixation on a specific face by the user. This type of zoom operation may also be used to enable closer inspection of scene features other than faces.

In one embodiment, facial detection is performed locally on the smartphone processor; the output of module 701 is then transmitted to a dedicated network server and subsequently processed there. In another embodiment, facial detection 701 and feature extraction 702 are performed locally on the smartphone processor. Facial feature data is then transmitted to a dedicated server or cloud computing processor for further analysis.

Data concerning recognized faces and facial expressions are relayed to the output generator module 704. Depending on the output resolution of the retinal stimulator, various embodiments of the output generator are possible. In one embodiment, a low-resolution output is produced, consisting of an alphanumeric representation of each recognized face. For example, a person named Abe in the user's address book may be represented by the letter "A". In another embodiment, a high-resolution avatar representation is generated. This avatar is a predefined symbolic depiction of the recognized face that is well known to the user, and may be obtained from the user's address book or other user database. Simple cartoon renderings of emotions are used to depict facial expressions.

In one embodiment, the People Aide superimposes a symbolic representation of faces and expressions onto live video generated by one or more of the Visual Sensors. In another embodiment, an abstract or symbolic representation alone is produced.

Figure 6:
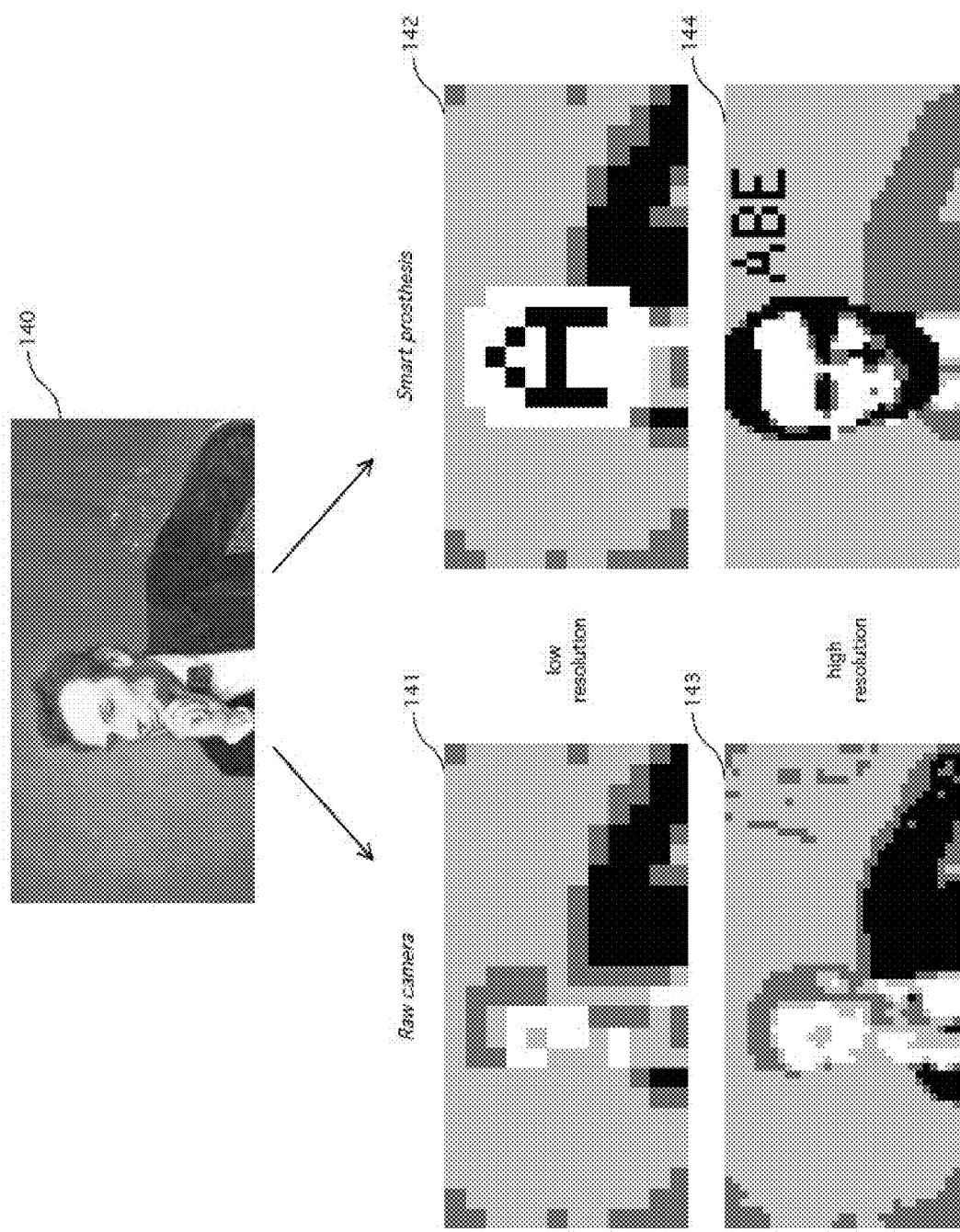
FIG. 6 shows a simulation of one manner in which an original image may be perceived by a user without and with a smart prosthesis system running the People Aide.

FIG. 6 gives an example of how the smart prosthesis improves the implant user experience while the People Aide is active. In this and the following figures, simulated examples for two scenarios are depicted: a low-resolution retinal implant containing 288 stimulating electrodes (a 24×12 array) and a high-resolution implant with 2048 electrodes (a 64×32 array). A stimulator output dynamic range of 4 levels is assumed in all the simulated examples shown (black, white, and 2 gray tones).

A real-world image 140 captured by one of the visual inputs results in the low-resolution image 141 if only raw camera pixels are relayed to the implant. No facial recognition can be expected from the user at this resolution. However, using the smart prosthesis, the user sees an abstracted image 142 containing the letter A to indicate that the People Aide has identified this face as Abe.

For a high-resolution stimulator, the raw camera image 143 still makes facial recognition by the user difficult. The smart prosthesis image 144, on the other hand, assigns a pre-defined and easily recognized symbolic image to this face, along with an alphanumeric caption of the person's name, for easy recognition by the user.

Reading Aide

The goal of the Reading Aide 71 is to detect written material and present it to the user in a fashion compatible with the limited spatial resolution of the retinal implant. This function converts any text into a clean, uncluttered, consistent display that is easily read by the implant user. A flowchart representative of the operations performed by an exemplary implementation of the Reading Aide 71 is shown in FIG. 7.

Figure 7:
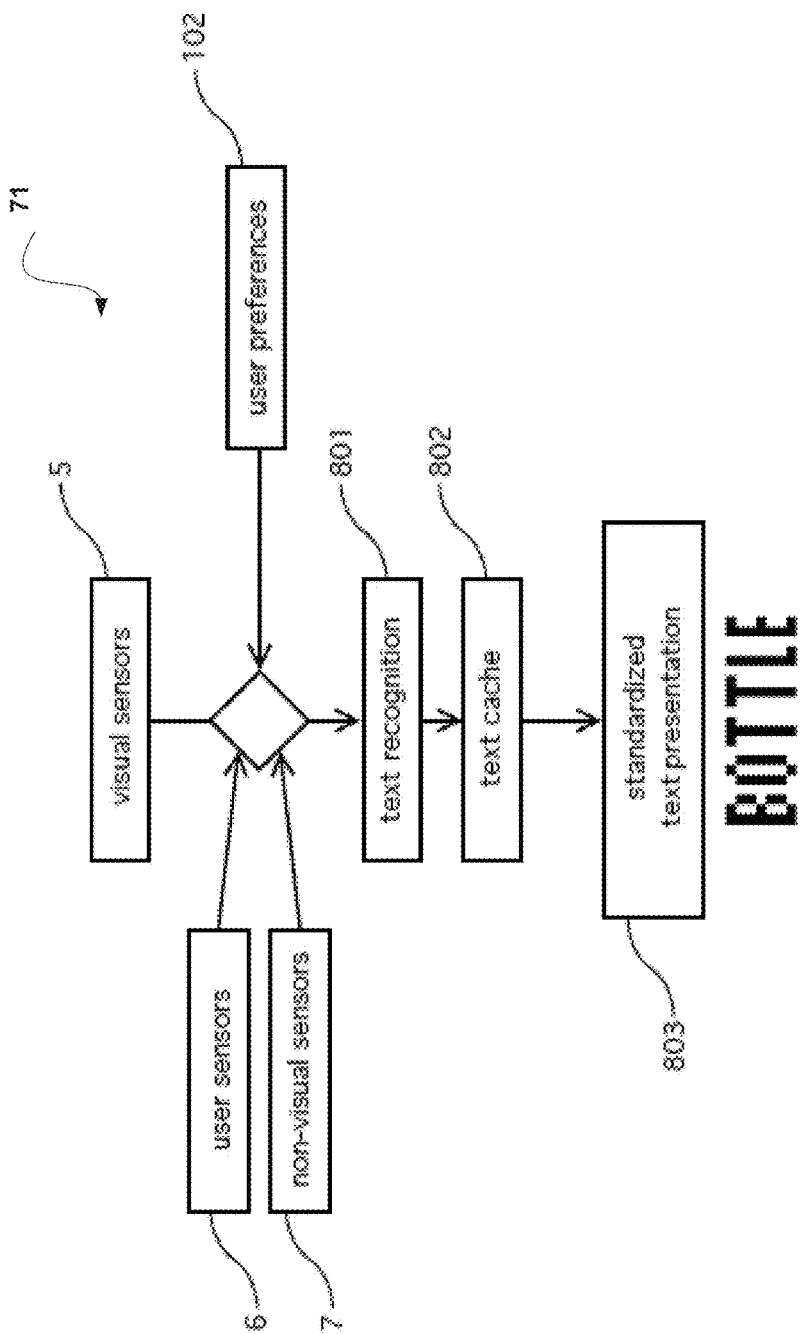
FIG. 7 is a flow chart depicting the function of the Reading Aide.

Referring to FIG. 7, visual input data 5 is subjected to real-time analysis for the extraction of letters, numbers, and symbols.

In one embodiment, the user interacts with this processing step by choosing which portion of the video stream to subject to the reading tool. In another embodiment, the text recognition process is launched automatically whenever readable material occupies the field of view of the camera. For example, after placing a book or magazine page within the field of view, the reading aide immediately initiates text detection. In a further embodiment, data from the user 6 and non-visual 7 sensors (for example, the gaze sensor 89 and accommodation sensor 90) is used to determine which part of the camera field of view the user is focusing on.

The text detection module 801 may, for example, use a standard optical character recognition (OCR) system and can be implemented using tools such as OCR-IT's OCR Cloud API or ExperVision's OpenRTK toolkit.

In one embodiment, the text detector 801 resides entirely on the smartphone processor. In this embodiment, a server connection is not required for this aide function. In another embodiment, video input data 5 is transmitted directly to a dedicated server for OCR processing.

Since the processed text typically contains many more text characters than can be displayed to the implant user at one time, it is typically cached in the smartphone local memory 802.

The text is then split into smaller text blocks for output 803 to the implant, depending on the resolution of the retinal stimulator. The font and size of text displayed to the implant user is optimized for readability, and is independent of the text properties of the original text. In one embodiment, a low-resolution output is generated, consisting of a single word or syllable. In another embodiment, a high-resolution output is generated, which may consist of one or more words. The user interacts with the display process by selecting the word presentation speed, as well as skipping forward or backward until all words or characters captured by the camera have been displayed.

Alternatively, an audio output is provided and the text is read to the user. This function may be implemented in a manner similar to that employed by dedicated reading machines for blind users, for example Nanopac's SARA scanner.

In one embodiment, the Reading Aide generates an augmented reality view of the world, with standardized text superimposed over live video. In another embodiment, the text output replaces all live video and fills the entire view of the implant user.

Figure 8:
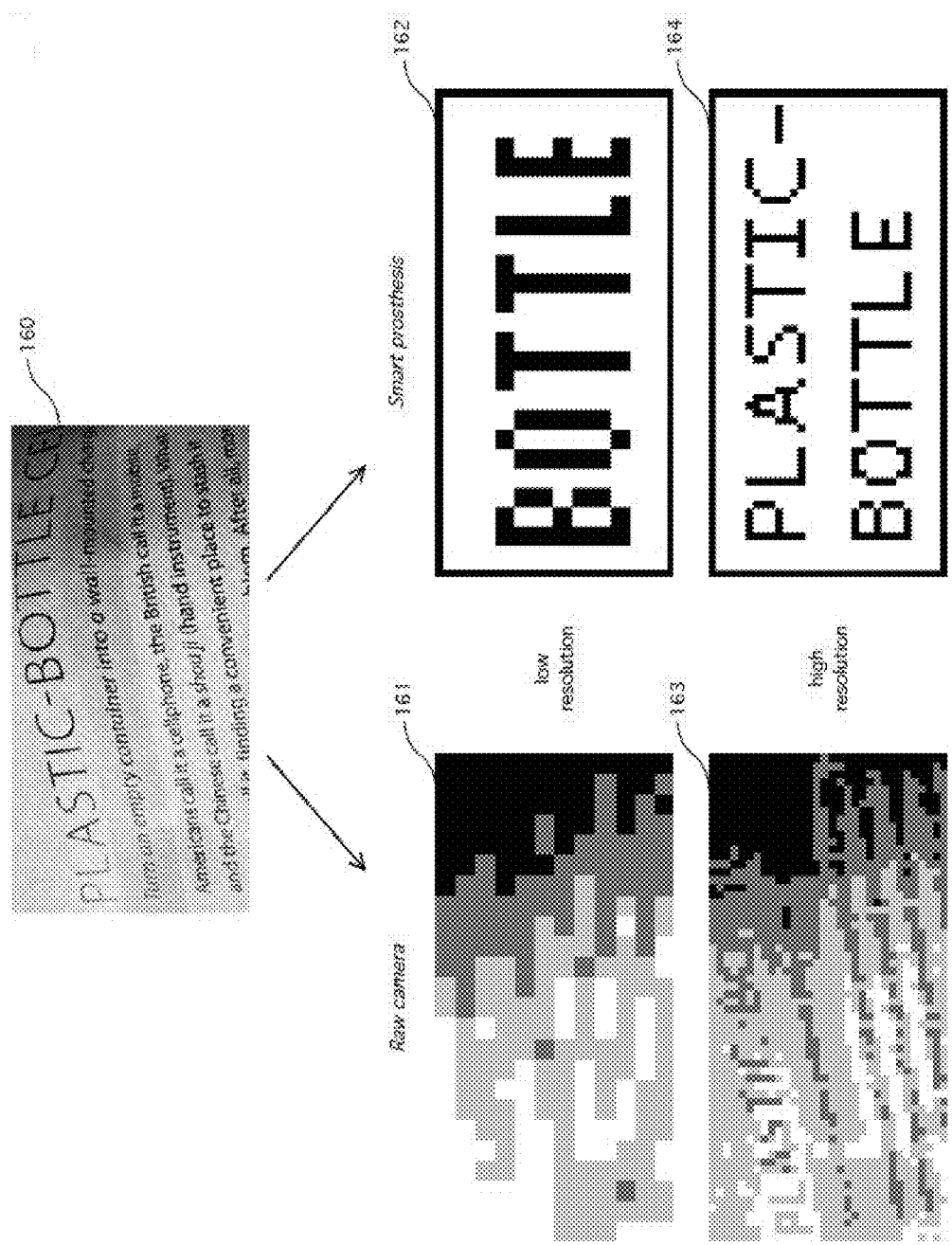
FIG. 8 shows a simulation of how an original image may be perceived by the user without and with a smart prosthesis system running the Reading Aide.

An example of how the Reading Aide may assist the implant user is shown in FIG. 8. A camera image 160 containing text with multiple fonts and styles is captured by one of the visual sensors. The raw pixelated camera image 161 is of no use to the user, but the smart prosthesis output image 162 displays legible text, one word at a time. A high-resolution stimulator image 163 may convey a few legible large letters, but using the smart prosthesis, all text in the input image is displayed to the user, including the smallest font text.

Navigation Aide

The primary function of the Navigation Aide 72 is to allow the user to easily negotiate a walking route to a specified geographic target. For this purpose, data from several sensors are combined to provide an abstracted view of the user's current location and route to the target destination. A flowchart representative of the operations performed by an exemplary implementation of the Navigation Aide 72 is shown in FIG. 9.

Figure 9:
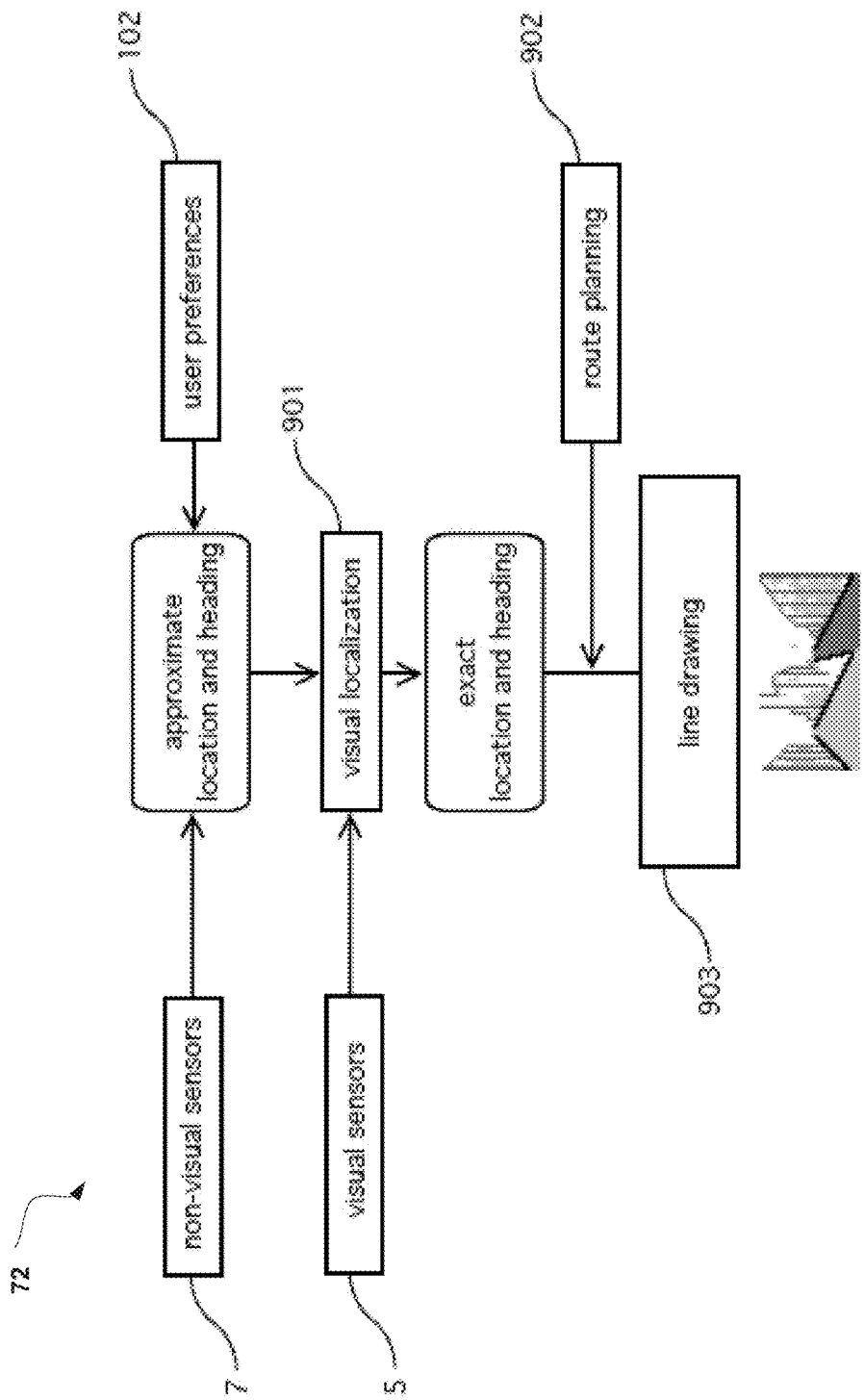
FIG. 9 is a flow chart depicting the function of the Navigation Aide.

Referring to FIG. 9, in a first step, data from the non-visual sensors 7 (in particular, compass 84 and GPS sensor 88) are used to determine the user's approximate geographic location and heading as GPS coordinates. This task may be carried out using a built-in location service on the smartphone, for example the iOS Core Location framework or the LocationManager system service for Android. The API is then used to translate the GPS coordinates into an approximate street address.

The approximate location and heading may then be subsequently refined to yield an exact user location and heading. To this end a method of visual localization 901 may be used, in which exact or more precise GPS coordinates are determined using images from the video stream produced by the Visual Sensors 5. In particular, this may be accomplished through a reverse lookup operation in which such images are matched with corresponding images within a repository of street-level image data (for example, Google Street View) associated with known GPS coordinates. Specifically, a query image derived from the image stream produced by the Visual Sensors 5 is matched against a GPS-tagged image data set; the location tag of the matched image is used to find the exact GPS location of the query image. In this application, the image search space is reduced significantly by access to the approximate location supplied by the first step.

Alternatively, a high accuracy GPS system replaces the reverse lookup process for the determination of exact user location. Handheld units with decimeter or centimeter accuracy are already on the market and are dropping rapidly in cost and size; an example is the Trimble GeoXH (6000). Such devices may be integrated into the video goggles 20 or the smartphone 15.

The exact user location and heading are then used in conjunction with route planning 902 to generate an abstracted output 903, depending on the resolution of the retinal stimulator. In one embodiment, a low-resolution output is produced, consisting mainly of lines indicating street outlines. At an intersection, different gray tones are used to indicate which street should be taken in order to proceed along the route to the target destination. In another embodiment, a high-resolution line drawing is generated, consisting of lines indicating street edges, building outlines, and route directions.

In one embodiment, the Navigation Aide generates an augmented reality view of the world, with line drawings superimposed over live video. This allows the user to see hazards and obstacles not present in the abstracted drawings of streets and buildings. In another embodiment, line drawings replace all live video, creating an alternate view of the world for the implant user.

Figure 10:
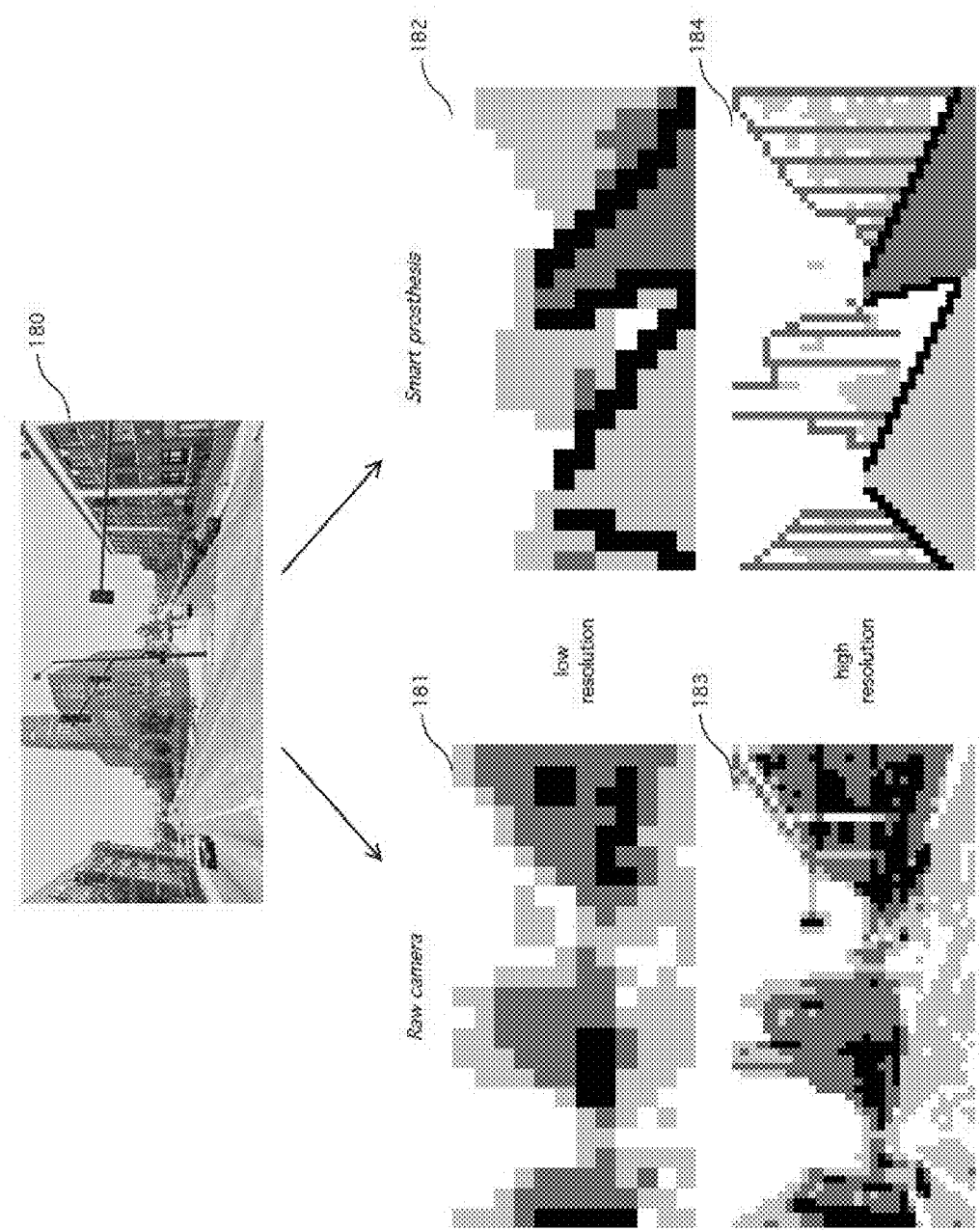
FIG. 10 shows a simulation of how an original image may be perceived by the user without and with a smart prosthesis system running the Navigation Aide.

FIG. 10 shows an example of the advantages presented by a smart prosthesis. A live video image 180 shows a typical street scene with roads, buildings, cars, and other distracting elements. The raw camera images 181 and 183 do not provide enough pertinent information for accurate navigation by the user. However, using the smart prosthesis images 182 and 184, the user can easily discern street outlines, buildings, and the preferred route to the destination target, indicated by a different shade of gray.

Environs Aide

A primary goal of the Environs Aide 73 is to provide a symbolic representation of the physical world in the immediate vicinity of the implant user in a manner that highlights important features, objects, and hazards. This function uses computer vision to break down the visual world into recognizable common objects and presents a simplified depiction of these objects to the user. A flowchart representative of the operations performed by an exemplary implementation of the Environs Aide 73 is shown in FIG. 11.

Figure 11:
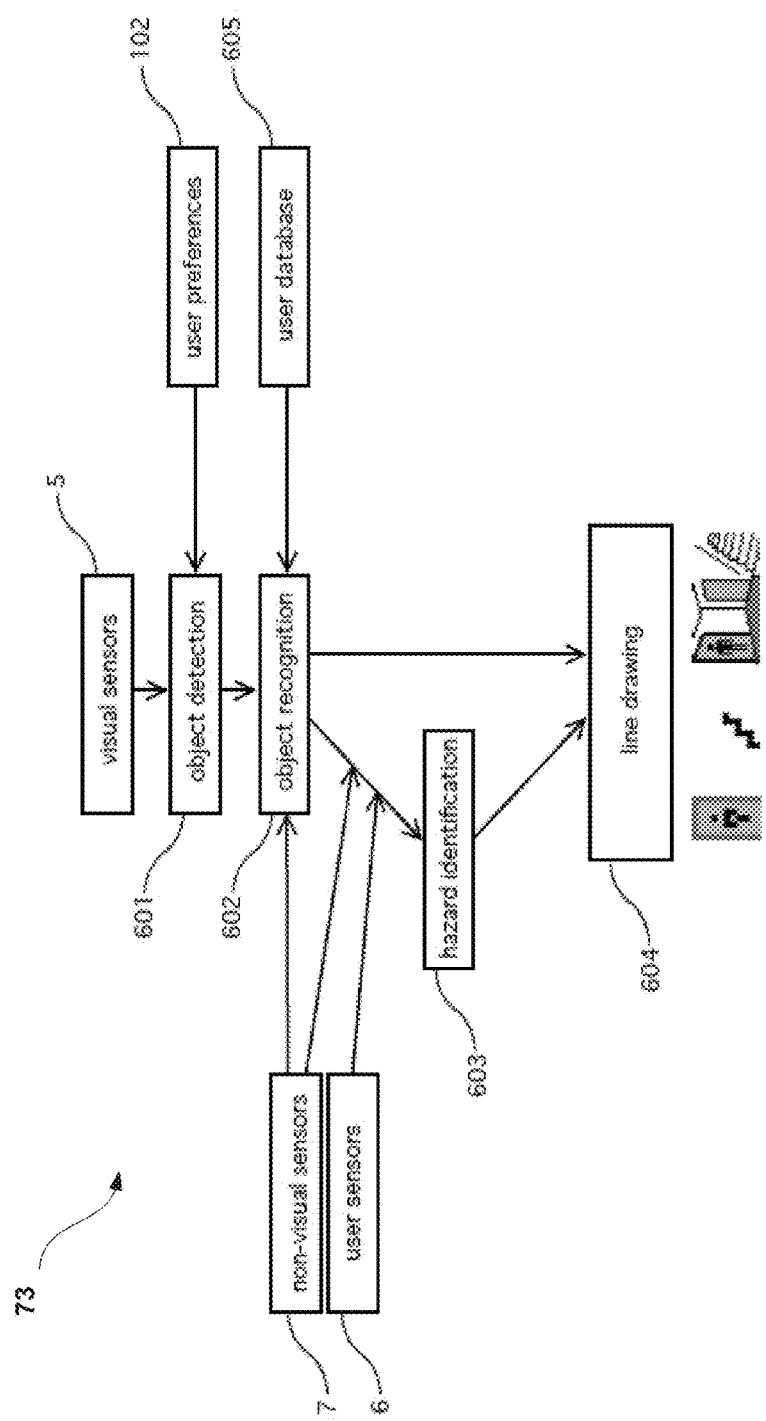
FIG. 11 is a flow chart depicting the function of the Environs Aide.

Referring to FIG. 11, images from the visual sensors 5 are analyzed in real-time to detect 601 and recognize 602 objects commonly encountered. Examples of such objects include doors, windows, stairs, and signs. Non-visual sensor 7 data (such as data from the 3D sensors 87) is used to aide in object segmentation and motion processing. Powerful cloud-based image recognition platforms already exist and can be leveraged by the smartphone application, for example the VisionIQ by IQ Engines, the Kooaba API, or Moodstock's Image Recognition API.

Objects and features of special significance to the users are stored in a user database 605. For examples, these can include furniture, signage, or known hazards in the user's home.

Special emphasis is placed on objects that could constitute a hazard to the user, such as gaps, obstacles, low-hanging lamps, steep staircases, tripping hazards, or furniture. A hazard identification module 603 determines whether an object might present a hazard to the user. For this task, data from the user 6 and non-visual sensors 7 are combined with recognized object location data (for example, depth data from the 3D sensors 87). The hazard identification module 603 may also use accelerometer data 85 to identify the user's current trajectory of motion to issue a collision warning.

In one embodiment, object detection 601, recognition 602, and identification 603 are performed locally on the smartphone processor. In this embodiment, a server connection is not required for this aide function, but the array of recognizable features is limited to those stored in the local user database 605. In another embodiment, object recognition 602 and hazard identification 603 are carried out using a dedicated network server. This enables access to large databases, making possible the identification of a vast multitude of features and objects.

Object identity, location, and hazard information are then used to generate an abstracted output 604, depending on stimulator resolution. In one embodiment, a low resolution output is produced, consisting of two-dimensional line drawings depicting in symbolic fashion the object location and identity. In another embodiment, a high-resolution output is generated, consisting of more detailed, three-dimensional line drawings. For example, the drawing may highlight the location and steepness of stairs, the position of furniture, or the outlines of a doorway. Hazardous objects may be highlighted by using a distinct gray tone or by a flashing symbols in the line drawings.

In one embodiment, the Environs Aide produces an augmented reality view of the world, with line drawings superimposed over live video. This allows the user to perceive nearby features and hazards in addition to those identified by the Environs Aide. In another embodiment, line drawings replace live video entirely.

Figure 12:
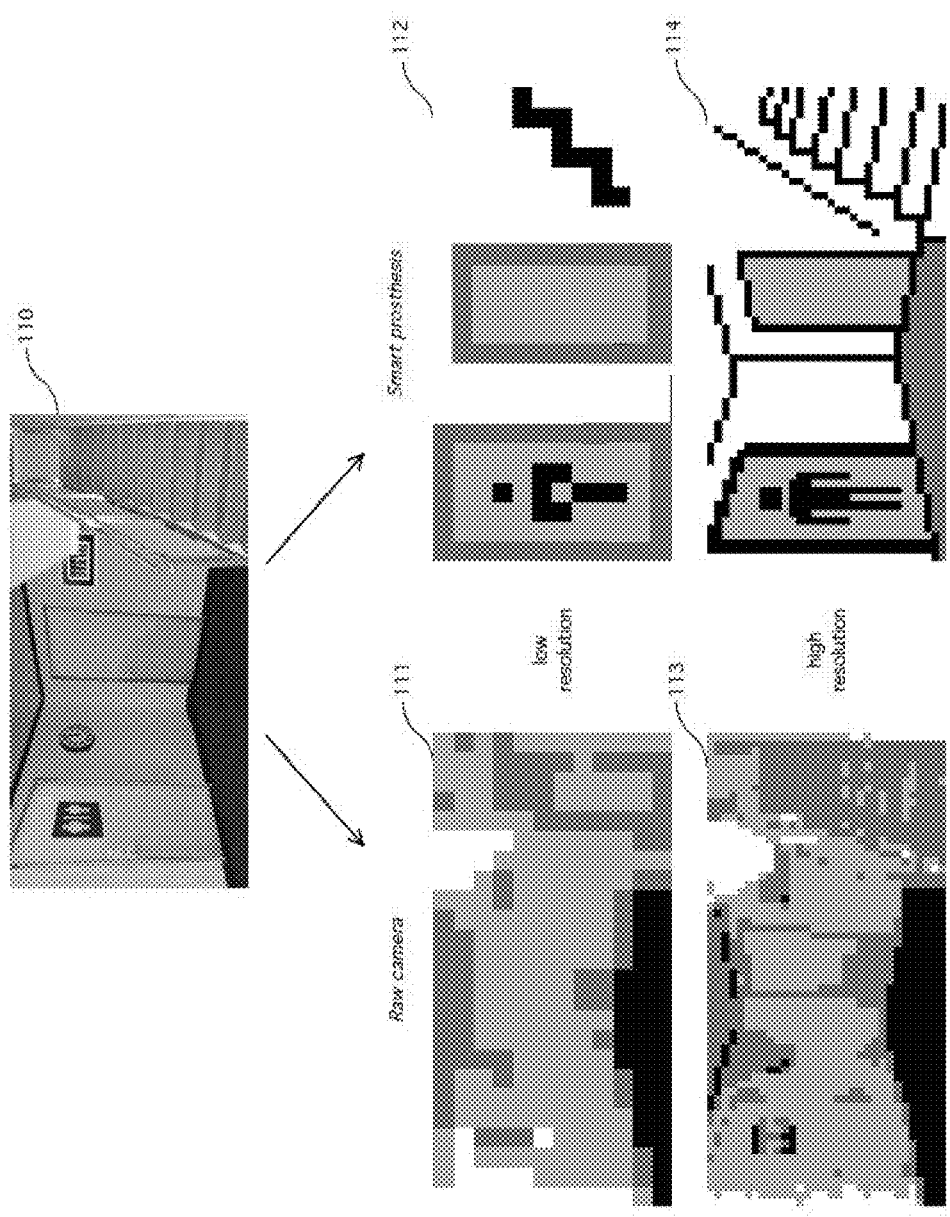
FIG. 12 shows a simulation of how an original image may be perceived by the user without and with a smart prosthesis system running the Environs Aide.

An example of the user experience using the Environs Aide is shown in FIG. 12. A video input image 110 contains various commonly encountered features. Neither the low-resolution 111 nor the high-resolution raw camera image 113 provide enough information about features and hazard to the user. The smart prosthesis output image 112, however, clearly depicts doors, signs, and the location of a staircase. The high-resolution output 114 additionally features three-dimensional cues and object details such as the precise location and steepness of the stairs.

Shopping Aide

A primary function of the Shopping Aide 74 is to assist the user in identifying objects commonly encountered during a shopping trip and paying using common paper currency. The aide recognizes grocery items and banknotes and presents these to the user in schematic form. A flowchart representative of the operations performed by an exemplary implementation of the Shopping Aide 74 is shown in FIG. 13.

Figure 13:
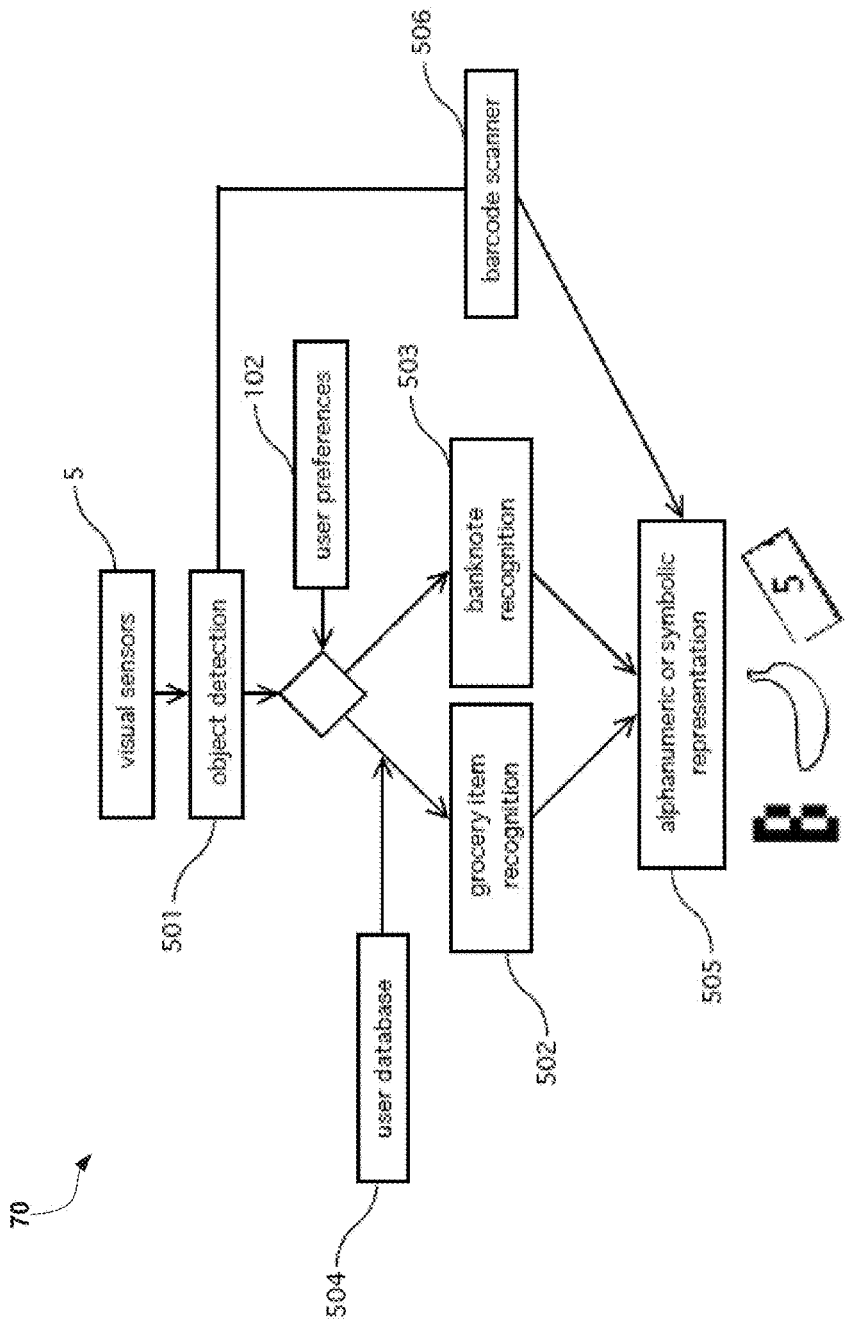
FIG. 13 is a flow chart depicting the function of the Shopping Aide.

Referring to FIG. 13, data from the visual sensors 5 is analyzed by an object detection module 501. The object recognition module 502 then identifies the objects in the video input. Examples include fruits and vegetables, milk cartons, or boxed items. Grocery items commonly purchased by the user are stored in a user database 504 for rapid retrieval. Cloud-based image recognition platforms already exist and can be incorporated into a smartphone application, for example the VisionIQ by IQ Engines, the Kooaba API, or Moodstock's Image Recognition API.

Using the barcode scanner module 506, the Shopping Aide enables the user to scan UPC bar codes present on packaged items and retrieve information on the scanned item. This task can be accomplished by incorporating bar code scanning APIs into the smartphone application, such as Scandit's UPC Product API or 3GVision's i-nigma Phone Barcode Reader SDK.

The banknote recognition module 503 identifies banknotes or other currency. Similar real-time currency recognition software already exists (for example, LookTel's Money Reader iPhone app or the Mobile Currency Reader for Android).

In one embodiment, object detection 501 and recognition 502-503 are performed locally on the smartphone processor. In this embodiment, a server connection is not required for this aide function, but the array of recognizable items is limited to those stored in the local user database 504. In another embodiment, object recognition 502-503 is carried out using a dedicated network server. This enables access to large databases, making possible the identification of a vast multitude of items.

The output 505 generated by the Shopping Aide consists of an alphanumeric or symbolic representation, depending on stimulator resolution. In one embodiment, a low resolution output is produced, consisting of a single letter or number. For example, "B" signifies Banana and "5" signifies a $5 banknote. In another embodiment, a high-resolution output is generated, consisting of symbols representing objects and banknotes. For example, an icon representing a banana or a rectangle depicting a $5 banknote is drawn.

The user may also launch the Shopping Aide in situations which do not involve shopping but require functions performed by the aide. For example, a barcode or QR-code may be scanned while reading a magazine, or banknotes in a wallet may be counted at home.

In one embodiment, the Shopping Aide superimposes a symbolic representation of items and banknotes onto live video. This allows the implant user to select additional objects to inspect as well as navigate through a store while using the Shopping Aide. In another embodiment, a symbolic representation alone is produced.

Figure 14:
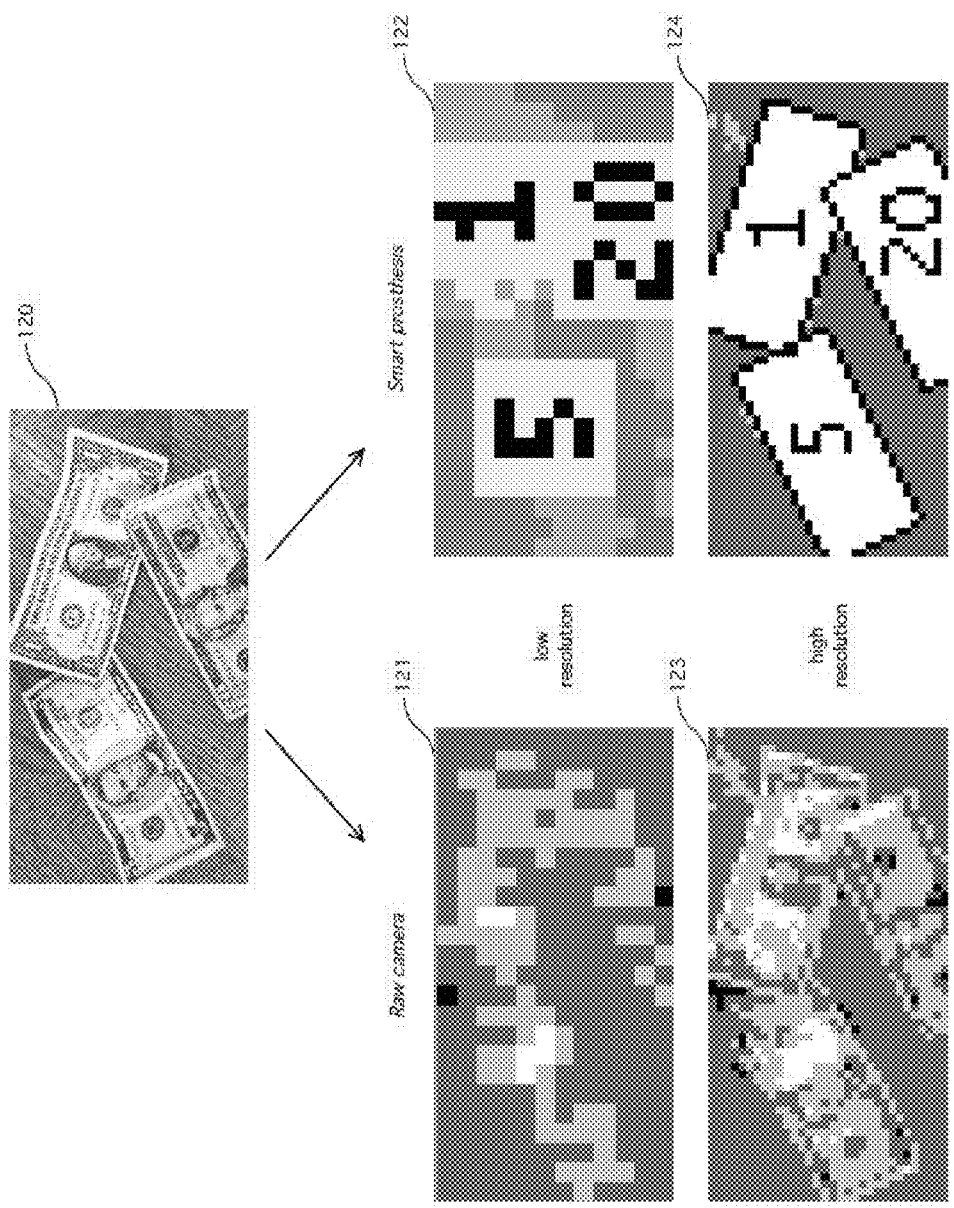
FIG. 14 shows a simulation of how an original image may be perceived by the user without and with a smart prosthesis system running the Shopping Aide.

FIG. 14 shows a demonstration of the banknote identification capabilities of the Shopping Aide. The video input 120 contains several banknotes. The dollar value on these banknotes cannot be identified from the raw pixelated camera images 121 and 123. In contrast, the smart prosthesis output images 122 and 124 display the location and value of each banknote to the user.

Figure 15:
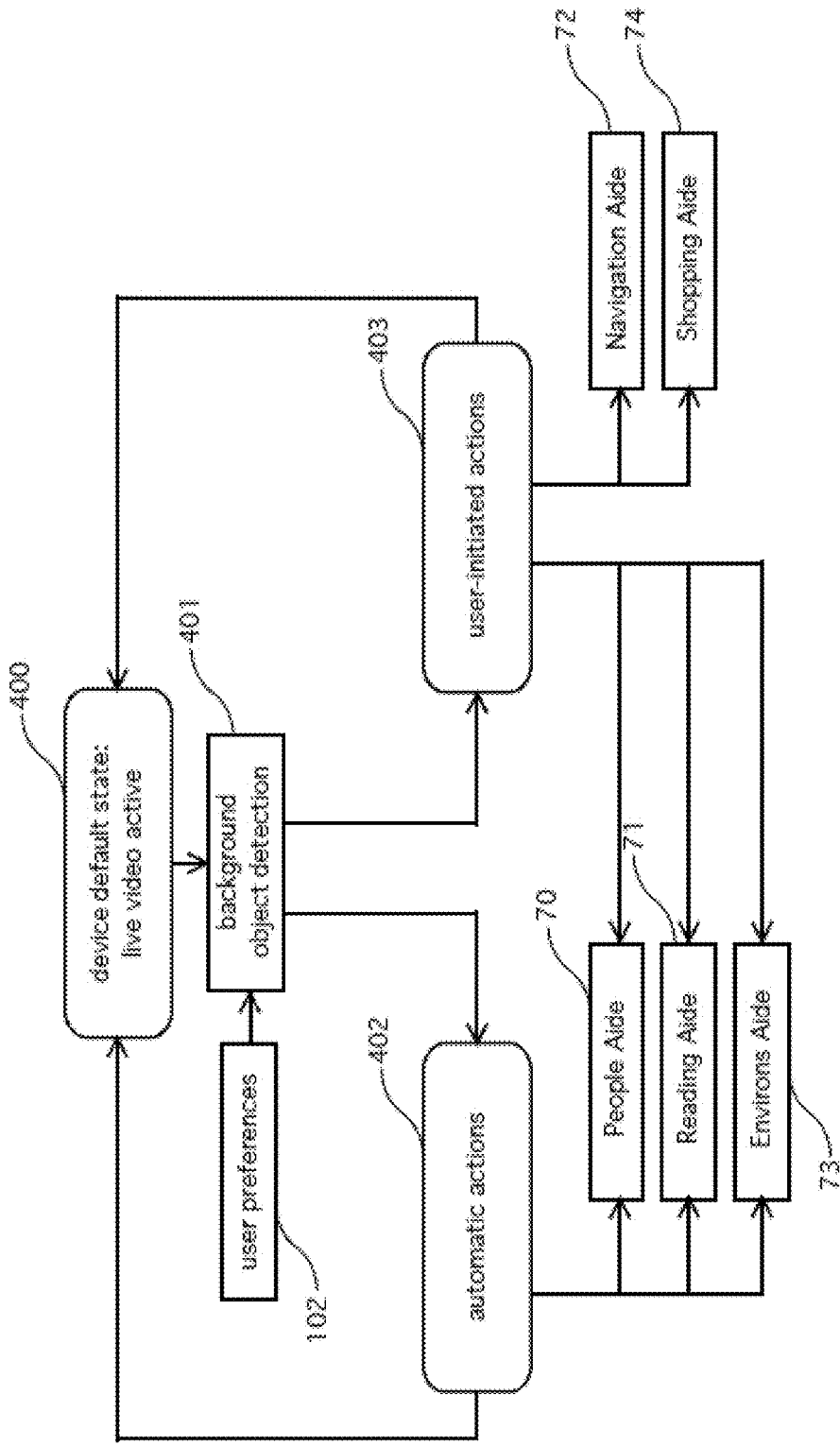
FIG. 15 is a flow chart depicting the flow of actions that typically occur during use of an embodiment of the smart prosthesis system.

FIG. 15 provides a flowchart representative of typical operation of the smart prosthesis in exemplary real-world scenarios. Specifically, FIG. 15 depicts a representative temporal flow of actions as the user views and interacts with the user's environment. In the absence of any aide functions being activated, the prosthesis relays a live video signal from the visual sensors to the user (400). A low-level background object detection module 401 continuously analyzes the video stream for the presence of various objects. The settings for background detection are customizable by the user 102. As mentioned above, scenarios that can trigger the automatic activation 402 of an aide function include detection of a face (People Aide 70), written text material (Reading Aide 71), or objects to be processed by the Environs Aide 73. The user can actively initiate (403) any of the aide functions, but the Navigation Aide 72 and the Shopping Aide 74 require user initiation since they rely on user data input. After termination of any aide function, the prosthesis output returns to its default state 400.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

In conclusion, embodiments in accordance with the disclosure provide, among other things, a system and method for automatic failure detection and anomaly detection. Those skilled in the art can readily recognize that numerous variations and substitutions may be made in the disclosed embodiments, their use and their configuration to achieve substantially the same results as achieved by the embodiments described herein. Accordingly, there is no intention to limit the claims to the disclosed exemplary forms. Many variations, modifications and alternative constructions fall within the scope and spirit of the disclosure as expressed in the claims.

What is claimed is:

1. A method of providing artificial vision to a visually-impaired user implanted with a visual prosthesis, the method comprising:
   producing an input image signal in response to optical input representative of a scene;
   recognizing, by processing the input image signal, at least one item within the scene;
   creating an abstract representation of the scene wherein the abstract representation includes a symbolic representation of the at least one item;
   generating augmented image data wherein the augmented image data includes at least a portion of the input image signal and abstracted data corresponding to the abstract representation; and
   providing, to the visual prosthesis, a signal including pixel values wherein the pixel values are based upon the augmented image data.

2. A method of assisting a visually-impaired user, the method comprising:
   receiving information relating to one or more actions performed by the user;
   determining, based upon the one or more actions, an aide function to be performed;
   receiving an input image signal generated in response to optical input representative of a scene;
   extracting, from the input image signal, item information relevant to the aide function;
   generating, based at least in part upon the item information, image data corresponding to an abstract representation of the scene; and
   providing, to a visual prosthesis of the user, a signal including pixel values wherein the pixel values are based upon the image data.

3. The method of claim 2 wherein the item information corresponds to at least one item within the scene, the generating including incorporating a symbolic representation of the at least one item within the abstract representation.

4. The method of claim 2 wherein the one or more actions relate to a gaze of the user.

5. The method of claim 2 wherein the one or more actions relate to blinking of at least one of the user's eyes.

6. The method of claim 2 wherein the one or more actions relate to use of a user input device.

7. A smart prosthesis, comprising:
   a processor;
   a video input device;
   a non-transitory machine readable medium including instructions for execution by the processor, the instructions comprising instructions for:
   receiving an input video signal produced by the video input device in response to optical input representative of a scene;
   recognizing, by processing the input video signal, at least one item within the scene;
   generating image data corresponding to an abstract representation of the scene wherein the abstract representation includes a symbolic representation of the at least one item; and
   providing, to a visual prosthesis of the user, an output signal including pixel values wherein the pixel values are based upon the image data.

8. The smart prosthesis of claim 7 wherein the at least one item comprises a face.

9. The smart prosthesis of claim 7 wherein the at least one item comprises an object.

10. The smart prosthesis of claim 7 wherein the at least one item comprises textual information.

11. The smart prosthesis of claim of claim 7 further including a network interface, the instructions for recognizing further include instructions for:
   transmitting, over a data connection established through the network interface, item information extracted from the input image signal, and
   receiving, over the data connection, item data relating to the symbolic representation.

12. The smart prosthesis of claim 7 wherein the instructions include instructions for configuring the smart prosthesis to perform at least one function of a plurality of functions in order to facilitate performance of an aide function.

13. The smart prosthesis of claim of claim 12 wherein the instructions for configuring include instructions for transitioning, in response to selection information received from the user, operation of the smart prosthesis from performing a default function to performing the at least one function.

14. The smart prosthesis of claim of claim 13 wherein the instructions for configuring include instructions for transitioning operation of the smart prosthesis from performing the at least one function to performing the default function upon completion of the aide function.

15. The smart prosthesis of claim of claim 7 further including a network interface, the instructions further including instructions for:
   transmitting, over a data connection established by the network interface, item information extracted from the input image signal, and
   receiving, over the data connection, item data wherein the item data relates to the at least one item.

16. The smart prosthesis of claim of claim 7 wherein the instructions for recognizing include instructions for:

receiving an indication of a region in the scene of interest to the user; and selecting and processing at least portions of the input image signal associated with the region.

17. The smart prosthesis of claim of claim 7 wherein the instructions for recognizing include instructions for:

receiving an indication of items of interest to the user; and processing the input image signal to identify at least one of the items of interest wherein the at least one of the items of interest corresponds to the at least one item.

18. The smart prosthesis of claim 7 wherein the instructions for providing image data further include instructions for replacing pixel data within the input image signal with abstract image information.

19. The smart prosthesis of claim 7 wherein the abstract image information comprises at least one of textual information, numeric information, line drawing information and cartoon information.

20. A smart prosthesis for use by a visually-impaired user, the smart prosthesis comprising:

a processor;

a non-transitory machine readable medium including instructions for execution by the processor, the instructions comprising instructions for:

receiving an input image signal produced in response to optical input representative of a scene;

recognizing, by processing the input image signal, at least one item within the scene;

generating image data corresponding to an abstract representation of the scene wherein the abstract representation includes a symbolic representation of the at least one item; and providing, to a visual prosthesis of the user, an output signal including pixel values wherein the pixel values are based upon the image data.

21. The smart prosthesis of claim 20 further including a video input device configured to generate the input image signal.

22. A smart prosthesis for use by a visually-impaired user, the smart prosthesis comprising:

a processor;

a non-transitory machine readable medium including instructions for execution by the processor, the instructions comprising instructions for:

configuring, in response to selection information received from the user, the smart prosthesis to perform least one function of a plurality of functions in order to facilitate performance of an aide function;

extracting, from an input image signal generated in response to optical input representative of a scene, item information relating to at least one item within the scene relevant to the aide function;

generating, by the smart prosthesis, image data corresponding to an abstract representation of the scene wherein the abstract representation includes a representation of the at least one item associated with the item information; and providing, to a visual prosthesis of the user, an output signal including pixel values wherein the pixel values are based upon the image data.

23. The smart prosthesis of claim 22 wherein the instructions for configuring include instructions for transitioning, in response to the selection information, operation of the smart prosthesis from performing a default function to performing the at least one function.

24. The smart prosthesis of claim 23 wherein the instructions for configuring include instructions for transitioning operation of the smart prosthesis from performing the at least one function to performing the default function upon completion of the aide function.

25. A smart prosthesis for assisting a visually-impaired user, the smart prosthesis comprising:

a processor;

a non-transitory machine readable medium including instructions for execution by the processor, the instructions comprising instructions for:

receiving information relating to one or more actions performed by the user;

determining, based upon the one or more actions, an aide function to be performed;

receiving an input image signal generated in response to optical input representative of a scene;

extracting, from the input image signal, item information relevant to the aide function;

generating, based at least in part upon the item information, image data corresponding to an abstract representation of the scene; and providing, to a visual prosthesis of the user, an output signal including pixel values wherein the pixel values are based upon the image data.

26. The smart prosthesis of claim 25 wherein the item information corresponds to at least one item within the scene, the instructions for generating further including instructions for incorporating a symbolic representation of the at least one item within the abstract representation.

27. The smart prosthesis of claim 25 wherein the instructions for generating further include instructions for replacing pixel information within the input image signal with abstract image information.

28. The smart prosthesis of claim 25 wherein the processor is included within a smartphone.

29. The smart prosthesis of claim 22 wherein the processor is included within a smartphone.

30. The method of claim 1, further including:

receiving information relating to one or more actions performed by the visually-impaired user;

determining, based upon the one or more actions, an aide function to be performed;

wherein the at least one item is relevant to the aide function.

31. The smart prosthesis of claim 7 wherein the instructions further include instructions for:

receiving information relating to one or more actions performed by the user;

determining, based upon the one or more actions, a visual task to be performed;

wherein the at least one item is relevant to the aide function.

32. The smart prosthesis of claim 20 wherein the instructions further include instructions for:

receiving information relating to one or more actions performed by the visually-impaired user;

determining, based upon the one or more actions, an aide function to be performed;

wherein the at least one item is relevant to the aide function.

33. The method of claim 1 wherein the signal includes pixel data from the input image signal.

34. The method of claim 2 wherein the signal includes pixel data from the input image signal.

* * * * *